United States Patent
Otera

(10) Patent No.: US 9,007,592 B2
(45) Date of Patent: Apr. 14, 2015

(54) GAS ANALYZER

(75) Inventor: Fumiaki Otera, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 89 days.

(21) Appl. No.: 13/552,437

(22) Filed: Jul. 18, 2012

(65) Prior Publication Data

US 2014/0022542 A1  Jan. 23, 2014

(51) Int. Cl.
G01N 21/61 (2006.01)
G01J 3/42 (2006.01)
G01N 21/39 (2006.01)
G01N 21/3504 (2014.01)
G01N 21/85 (2006.01)

(52) U.S. Cl.
CPC . *G01J 3/42* (2013.01); *G01N 21/61* (2013.01); *G01N 21/39* (2013.01); *G01N 21/3504* (2013.01); *G01N 21/85* (2013.01)

(58) Field of Classification Search
None
See application file for complete search history.

(56) References Cited

U.S. PATENT DOCUMENTS

2002/0180991 A1* 12/2002 Takoudis et al. .............. 356/630

FOREIGN PATENT DOCUMENTS

| JP | 59058339 A | 4/1984 |
| JP | 05-099845 | 4/1993 |
| JP | 2006125919 A | 5/2006 |
| WO | WO-8607455 A1 | 12/1986 |

OTHER PUBLICATIONS

Japanese Office Action dated May 28, 2013 for corresponding Japanese Patent Application No. 2010-008950, and the English translation of "Reason for Rejection".

* cited by examiner

*Primary Examiner* — Kara E Geisel
*Assistant Examiner* — Amanda Merlino
(74) *Attorney, Agent, or Firm* — Morgan, Lewis & Bockius LLP

(57) ABSTRACT

A gas analyzer is capable of detecting abnormality of a measurement environment without using either or both of a pressure sensor and a gas temperature sensor. The gas analyzer creates absorption spectra from transmitted light intensity of laser beams applied to gas for measuring the amount of spread W and compares the amount of spread against a threshold D. The amount of spread of the absorption spectra does not depend on pressure if the pressure of the gas to be measured falls within a high-vacuum region, and monotonously increases with increased pressure if the pressure of the gas to be measured is higher than the high-vacuum region. Thus, if W>D, it is determined that the measurement environment does not form a high-vacuum region and abnormality is transmitted to the outside. In all other cases, the measurement environment is deemed to form a high-vacuum region, and partial pressure is calculated.

6 Claims, 13 Drawing Sheets

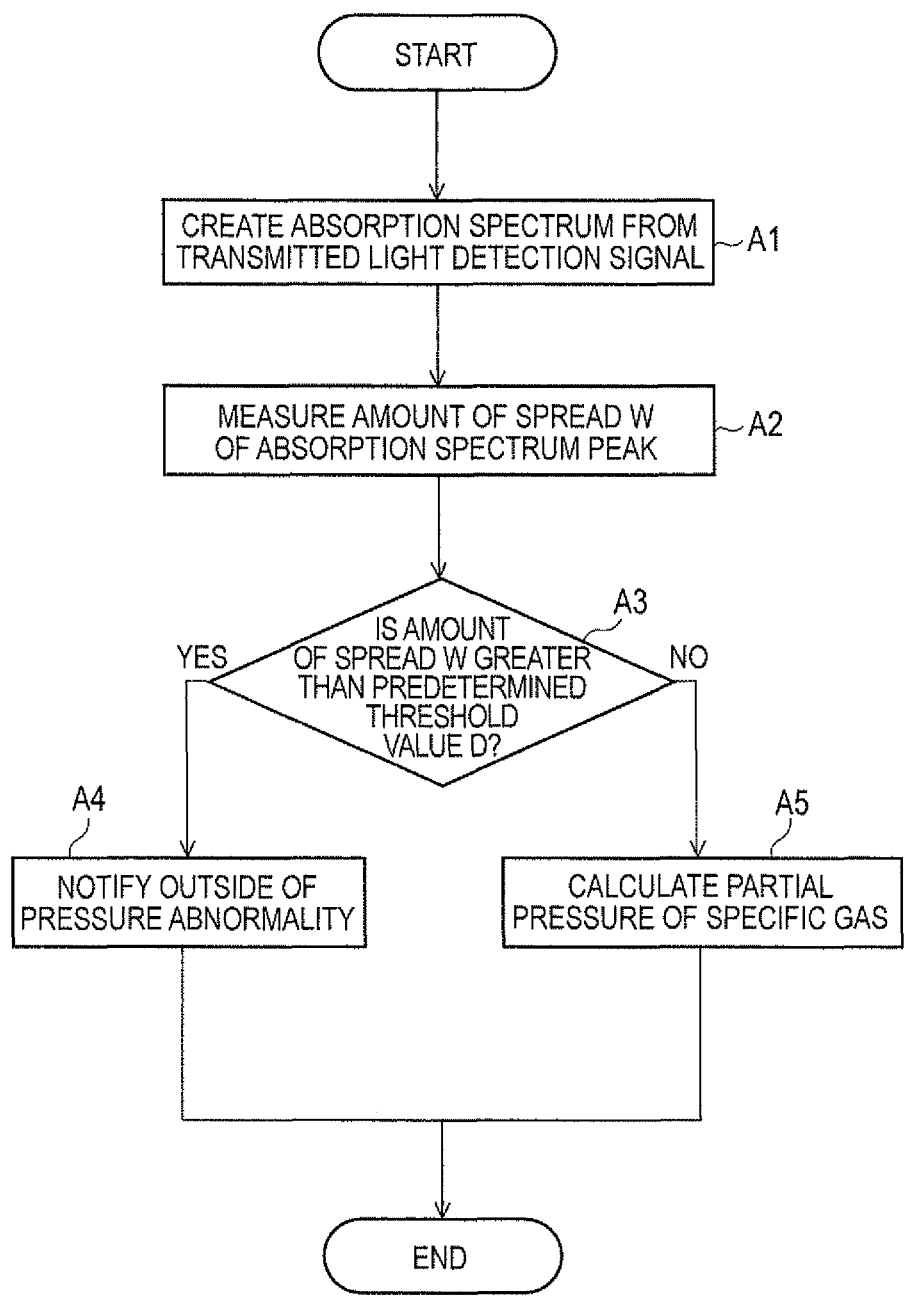

US 9,007,592 B2

GAS ANALYZER

TECHNICAL FIELD

The present invention relates to a gas analyzer that uses laser absorption spectroscopy for measuring the partial pressure of a specific gas in a gas to be measured.

BACKGROUND ART

A method for measuring the partial pressure of a specific gas in a gas to be measured that has been proposed in recent years is laser absorption spectroscopy that uses a wavelength variable laser (see, for example, Patent Literature 1). With this method, a sample cell into which a gas to be measured has been introduced is irradiated with a laser beam while changing its wavelength within a predetermined wavelength range. The laser beam that has been transmitted through the gas to be measured is analyzed, and a partial pressure of a specific gas is calculated from the amount of absorption by the specific gas in the gas to be measured. Because there is no contact between the gas to be measured and the light source or the photoreceptors, this device offers advantages such as measurements being possible without disrupting the field (non-contact measurement) and the extremely quick response time (high time-resolution).

FIG. 1 shows one example of a gas analyzer of the previous type that uses laser absorption spectroscopy. With this gas analyzer, a sample cell 1 is positioned to be substantially orthogonal to the direction of gas flow path 2 through which the gas to be measured flows. Reflection mirrors 3 and 4, which oppose each other, are disposed at either ends of sample cell 1. A transparent window 5 through which only light can pass is disposed on reflection mirror 3. An optical chamber 6 with a substantially sealed structure and whose atmosphere is at substantially atmospheric pressure is disposed outside of sample cell 1 with said transparent window 5 interposed in between. Contained within the optical chamber 6 are a wavelength variable laser 7 and a photodetector 8.

A pressure sensor 9 and a gas temperature sensor 10 are installed in sample cell 1, the pressure sensor 9 measuring the pressure (total pressure) of the gas to be measured and the gas temperature sensor 10 measuring the temperature of the gas to be measured.

With the gas analyzer shown in FIG. 1, under the control of laser controller 11, wavelength variable laser 7 emits a laser beam while varying its wavelength within a predetermined wavelength range that includes the center wavelength of the absorption spectrum of a specific gas. The laser beam that is emitted by wavelength variable laser 7 passes through transparent window 5 and enters sample cell 1 and makes round-trips between reflection mirrors 3 and 4 during which the laser beam is absorbed by a specific gas in the gas to be measured. The laser beam then travels through transparent window 5 and returns into optical chamber 6 where the intensity of the transmitted light is measured by photodetector 8.

The transmission light intensity measured by photodetector 8 and the pressure and the temperature of the gas to be measured—measured by pressure sensor 9 and gas temperature sensor 10—undergo signal processing such as analog/digital conversion and noise elimination and are input to computation unit 12 where the partial pressure of the specific gas is calculated using a predetermined computational process.

Patent Literature 1: Unexamined Patent Application Publication No. H05-99845

Non-Patent Literature 1: J. J. Olivero and R. L. Longbothum, "Empirical Fits to the Voigt Line Width: A Brief Review," Journal of Quantitative Spectroscopy and Radiative Transfer, Vol. 17 (1977), pp. 233-236.

SUMMARY OF THE INVENTION

As afore-described, in addition to the laser measurement system, gas analyzers of the previous type that use laser absorption spectroscopy are equipped with a pressure sensor and a gas temperature sensor, which concurrently measure the pressure and temperature of the gas to be measured while the intensity of the transmitted light is measured.

Another example of the use of a gas analyzer is in a predetermined high-vacuum region such as for measuring the partial pressure in an exhaust line of a semiconductor process device. For such limited purposes, in calculating the partial pressure of a specific gas, what is important is not the precise pressure of the gas to be measured but rather whether the measurement environment is at a high vacuum or not. With such use, a pressure sensor is not always necessary. Also, if the temperature of the gas to be measured is known in advance and is kept substantially constant, a gas temperature sensor is not always necessary.

However, with a configuration wherein a gas temperature sensor or a pressure sensor is not provided, rapid changes in pressure or temperature of the gas to be measured caused by some abnormality in the measurement environment will go undetected, raising the risk that an erroneous partial pressure value will be output as the correct measurement result. With previous gas analyzers, even if the use may be limited and measuring the pressure or temperature of the gas to be measured is not always unnecessary, a pressure sensor and a gas temperature sensor were provided for detecting abnormalities in the measurement environment. However, pressure sensors and gas temperature sensors are generally not inexpensive, and they occupy physical space.

The problem to be solved by the present invention is to provide a gas analyzer capable of detecting abnormalities of a measurement environment without using either or both of a pressure sensor and a gas temperature sensor.

The gas analyzer according to the present invention that was made to solve the afore-described problem includes: an irradiation means for irradiating a laser beam onto a gas to be measured; a laser control means for controlling the laser irradiation means so that the emission wavelength of the laser beam changes over a predetermined wavelength range that includes the center wavelength of the absorption spectrum of a specific gas that is included in the gas to be measured; and a light-receiving means for receiving the laser beam that has been transmitted through the gas to be measured; and further including:

a) a spectrum creation means for creating an absorption spectrum from detection signals of the laser beam received by the light-receiving means;

b) an amount-of-spread measurement means for measuring the amount of spread of a peak of the absorption spectrum; and c) a determination means for determining whether or not the amount of spread falls within a predetermined range.

The inventor of the present application focused on the fact that the shape of an absorption spectrum depends on both pressure and temperature when the pressure of a gas to be measured is within a low-vacuum region (e.g., approximately 1 Torr or more) and that the shape of the peak of the absorption spectrum depends solely on temperature and not on pressure when the pressure of the gas to be measured is in a high-vacuum region (e.g., approximately no more than 1 Torr). With the gas analyzer according to the present invention, an absorption spectrum is created from detection signals of a laser beam. The amount of spread represented by such values as half-width at half-maximum or full-width at half-maximum of the absorption spectrum are constantly measured to monitor whether or not the pressure of the gas to be measured falls within a high-vacuum region. By so doing, a pressure sensor can be eliminated from the device configuration, thus lowering the cost and the size of the device.

Furthermore, the gas analyzer according to the present invention can also be used for detecting abnormalities in gas temperature in a measurement environment where the gas temperature is known in advance and remains constant but the pressure of the gas to be measured changes from atmospheric pressure to a high-vacuum region. With such use, because the gas analyzer according to the present invention allows a gas temperature sensor to be eliminated from a device configuration, the cost and the size of the device can be reduced as afore-described.

Furthermore, if the pressure of the gas to be measured is in a high-vacuum region and the gas temperature is known in advance and is constant, both the pressure sensor and the gas temperature sensor can be eliminated from the device configuration. In that case, the gas analyzer according to the present invention can detect abnormalities in either the pressure or the temperature of the gas to be measured.

BRIEF DESCRIPTION OF THE FIGURES

FIG. 6 is a flowchart showing the process flow in the computation unit of the first embodiment as a moisture measurement apparatus.

DETAILED DESCRIPTION OF THE INVENTION

Figure 1:
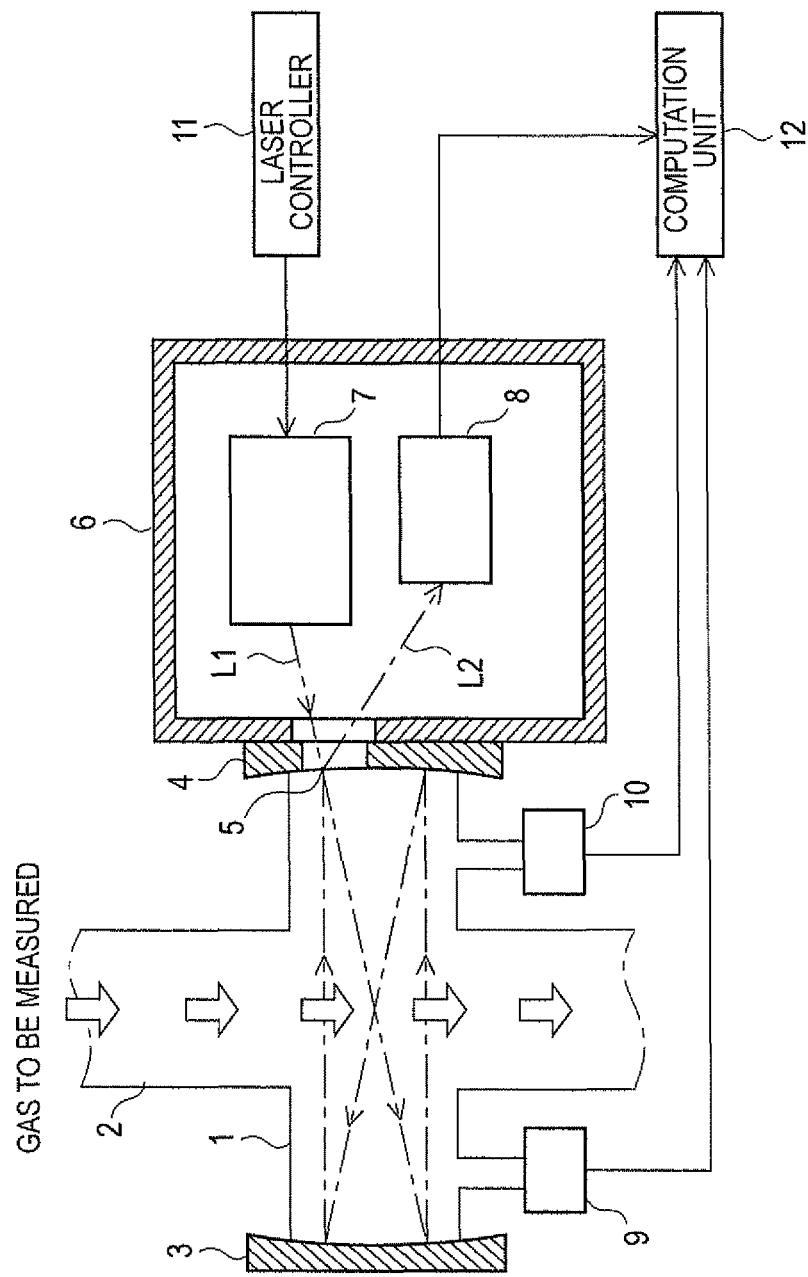
FIG. 1 shows a schematic view of a previous gas analyzer.

The general theory of laser absorption spectroscopy is first described. Let $I_0(\nu)$ and $I(\nu)$ respectively represent the intensity of a laser beam before and after absorption by a specific gas in a gas to be measured at a certain frequency $\nu$, and let the amount of absorption be represented by:

$$A(\nu)=\ln(I_0(\nu)/I(\nu)) \qquad (1)$$

The following equation then holds based on the Lambert-Beer Law.

$$A(\nu)=P_S \times L \times S(T) \times K(\nu)/(k_B T) \qquad (2)$$

Here, $P_S$ represents the partial pressure of the specific gas; L the length of the optical path passing through the gas to be measured; S(T) the absorption linear intensity, which is a function of gas temperature T; $K(\nu)$ the absorption property function that represents the shape of the peak of the absorption spectrum (absorption amount A spectrum); and $k_B$ the Boltzmann constant.

The behavior of the absorption property function $K(\nu)$ changes depending on the pressure region of the gas to be measured. For example, if the pressure of the gas to be measured is in a pressure region that is close to atmospheric pressure, the effect of the collision among gas molecules becomes dominant, and the absorption property function $K(\nu)$ is represented by the following Lorentz function:

$$K(\nu)=\gamma_L/[\pi\{(\nu-\nu_0)^2+\gamma_L^2\}] \qquad (3)$$

Here, $\nu_0$ is the center frequency of the absorption spectrum. $\gamma_L$ represents the half-width at half-maximum of $K(\nu)$ and $A(\nu)$ and is referred to as the Lorents width. The Lorents width $\gamma_L$ can be approximated by the following equation:

$$\gamma_L=\gamma_{L0}(P/P_0)(T_0/T)^\alpha \qquad (4)$$

Here, P represents the pressure (total pressure) of the gas to be measured, T the temperature of the gas to be measured, $\gamma_{L0}$ the half-width at half-maximum of $A(\nu)$ and $K(\nu)$ at standard condition (standard pressure $P_0$ and standard temperature $T_0$), and $\alpha$ a Lorents width temperature coefficient.

Equations (3) and (4) show that the shape of the absorption spectrum peak depends on the pressure and temperature of the gas to be measured. It is also evident that, with gases whose $\gamma_{L0}$ and $\alpha$ are known in advance, $K(\nu)$ can be calculated by measuring the pressure and temperature of the gas to be measured.

The absorption linear intensity S(T) can be approximated by multiplying the absorption linear intensity $S(T_0)$ at the standard condition by a correction term that relates to temperature T.

Equation 1

$$S(T) = S(T_0)\frac{Q(T_0)}{Q(T)}\frac{1-\exp\left(-\dfrac{hc\nu_0}{k_B T}\right)\exp\left(-\dfrac{hcE_j}{k_B T}\right)}{1-\exp\left(-\dfrac{hc\nu_0}{k_B T_0}\right)\exp\left(-\dfrac{hcE_j}{k_B T_0}\right)} \qquad (5)$$

Here, h represents the Planck constant, c the speed of light, $E_j$ the pre-transition energy level of the absorption line, and Q the partition function. Therefore, with a specific gas whose $S(T_0)$, $E_j$ and Q are known in advance, the absorption linear intensity S(T) can be calculated from the measured temperature of the gas to be measured.

As afore-described, by measuring the pressure and the temperature of the gas to be measured, the absorption property function K(ν) and absorption linear intensity S(T) can be calculated for specific gases whose $γ_{L0}$, α, $S(T_0)$, $E_j$ and Q are known. Furthermore, since the optical path length L is known, it is possible to calculate partial pressure $P_S$ of the specific gas by measuring the amount of absorption A at a predetermined frequency ν (e.g., at absorption center frequency $ν_0$).

On the other hand, in extremely low pressure regions, the spread of the absorption spectrum peak will become narrower than the afore-described Lorentz function by a single-digit factor to several double-digit factor. In such a pressure region, the spread of the absorption spectrum is primarily determined by the Doppler effect, and the absorption property function K(ν) is represented by the following Gaussian function.

$$K(ν)=1/[γ_{ED}×π^{1/2}×\exp\{(ν-ν_0)/γ_{E0}\}^2] \quad (6)$$

$γ_{ED}$ in equation (6) is referred to as the Doppler width and represents the half-width at half-maximum of A(ν) and K(ν) at a high-vacuum region. Here, $γ_{ED}$ is represented by the following equation as a function of molecular weight M of the specific gas:

$$γ_{ED}=ν_0/c×(2k_BT/M)^{1/2} \quad (7)$$

Equation (7) shows that $γ_{ED}$ does not depend on the pressure of the gas to be measured. This means that for a specific predetermined high-vacuum region, there is no need to measure the pressure of the gas to be measured to calculate the partial pressure of a specific gas.

For a pressure region falling between atmospheric pressure and a high-vacuum region, the absorption property function K(ν) is represented by a convolution function of the Lorentz function represented by equation (3) and the Gaussian function represented by equation (6). Furthermore, half-width at half-maximum $γ_V$ of the absorption amount A(ν) and absorption property function K(ν) in the intermediate pressure region is often approximated and represented by the following equation (Non-Patent Literature 1).

$$γ_V=0.5346γ_L+\{0.2166γ_L^2+\ln(2)×γ_{ED}^2\}^{1/2} \quad (8)$$

Here, $γ_V$ is referred to as the Voigt width. As equation (8) shows, since $γ_V$ includes $γ_L$, it is clear that in an intermediate pressure region, unlike in a high-vacuum region, it is necessary to measure the pressure of the gas to be measured in order to measure the partial pressure of a specific gas.

Figure 2:
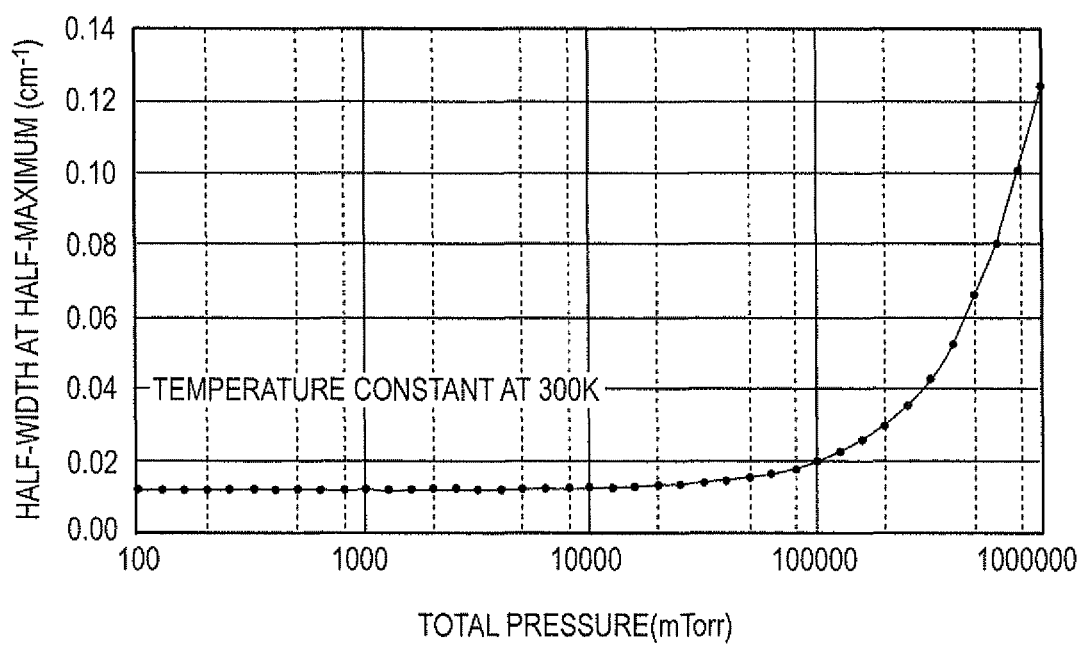
FIG. 2 is a graph showing the relationship between the pressure of a gas to be measured and the half-width at half-maximum of an absorption spectrum.

As shown above, in an intermediate pressure region and in a pressure region close to atmospheric pressure, the half-width at half-maximum and peak shape of the absorption spectrum depend on both pressure and temperature while they depend only on temperature in a high-vacuum region. In fact, the result shown in FIG. 2 was experimentally obtained when half-width at half-maximum of absorption property function K(ν) was plotted as a function of the pressure of the gas to be measured while holding the type and temperature of the gas to be measured constant. The graph shown in FIG. 2 shows that in a pressure region above approximately 1 Torr, half-width at half-maximum changes as a function of pressure while in a high-vacuum region of less than approximately 1 Torr, half-width at half-maximum does not depend on pressure.

The present invention uses the fact that, in a high-vacuum region, measuring the pressure of the gas to be measured is unnecessary for measuring the partial pressure of a specific gas. By restricting the measurement environment to a high-vacuum region of less than approximately 1 Torr, a pressure sensor is eliminated from the configuration of the gas analyzer. A gas analyzer according to the present invention is configured so that if the pressure of the gas to be measured is higher than a high-vacuum region, this is detected as an abnormality of the measurement environment. This increases the reliability of the partial pressure that is measured and reduces the size and cost of the device.

Embodiment 1

A first embodiment of a gas analyzer according to the present invention as a moisture measurement apparatus is described next with reference to figures.

Figure 3:
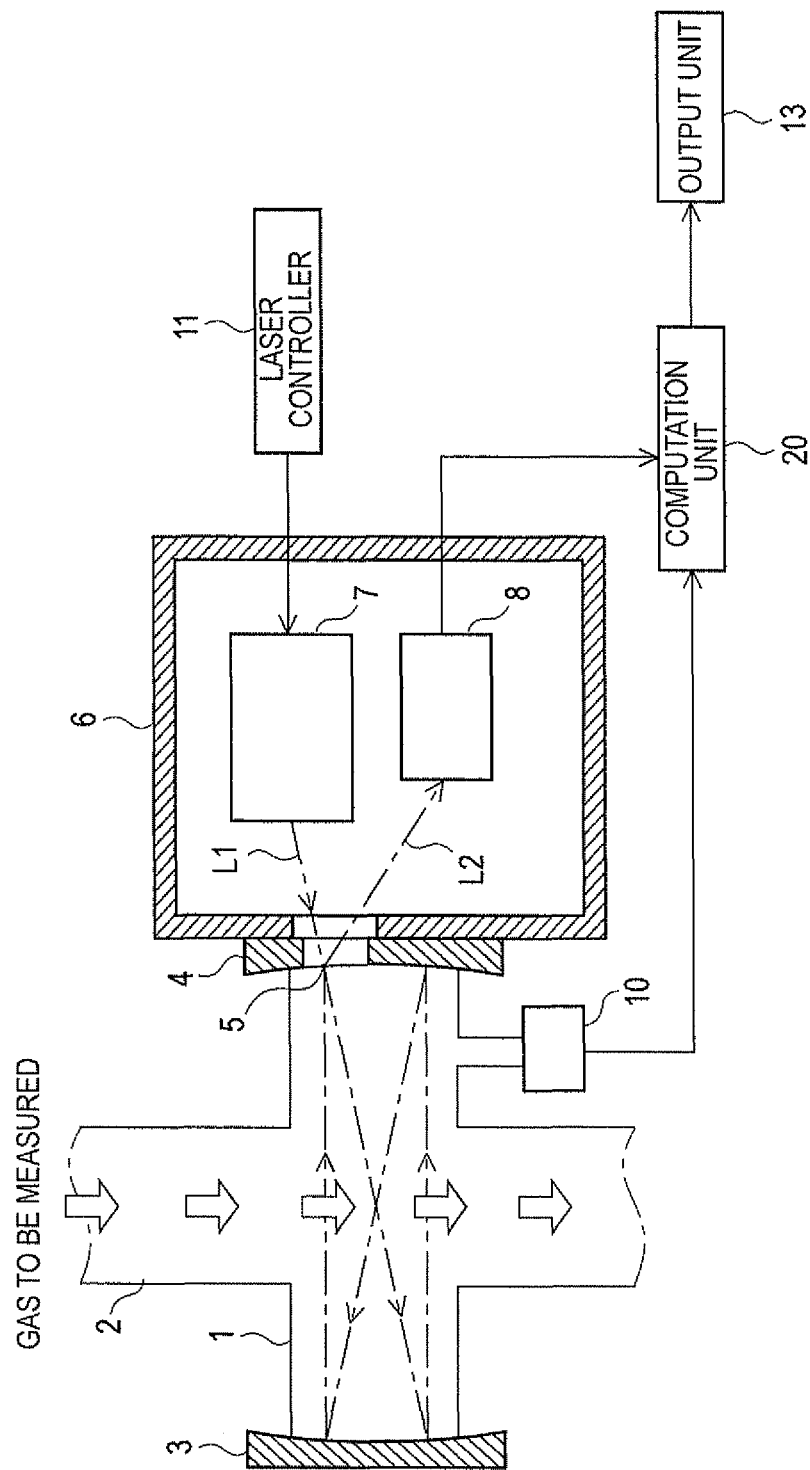
FIG. 3 shows a schematic view of a first embodiment of a gas analyzer according to the present invention as a moisture measurement apparatus.

FIG. 3 shows a schematic view of the present embodiment as a moisture measurement apparatus. The measurement optical system of the moisture measurement apparatus is the same as that described above for a gas measurement apparatus of the previous type shown in FIG. 1. In other words, the measurement optical system includes a gas flow path 2 through which the gas to be measured flows, a sample cell 1 that is positioned in gas flow path 2 to be substantially orthogonal to the direction of gas flow path 2, reflection mirrors 3 and 4, which oppose each other that are disposed at either ends of sample cell 1, a transparent window 5 through which only light can pass that is disposed on reflection mirror 3, an optical chamber 6 with a substantially sealed structure and whose atmosphere is at substantially atmospheric pressure that is disposed outside of sample cell 1 with said transparent window 5 interposed in between, wavelength variable laser (laser irradiation unit) 7 whose emission wavelength is controllable by laser controller 11 that is housed within optical chamber 6, and a photodetector (photoreceptor) 8, which is also housed within optical chamber 6 for measuring the intensity of the absorbed light.

Usable as wavelength variable laser 7 is a DFB (distributed feedback) type laser that emits at 1.3 μm, which is included in the absorption spectrum of water molecules. In addition to this laser, any wavelength variable laser that emits at a wavelength included within the absorption spectrum of water molecules can be used. Needless to say, to measure the partial pressure of a specific gas other than water, a wavelength variable laser that emits at a wavelength that is included in the absorption spectrum of the particular specific gas is used.

Figure 4:
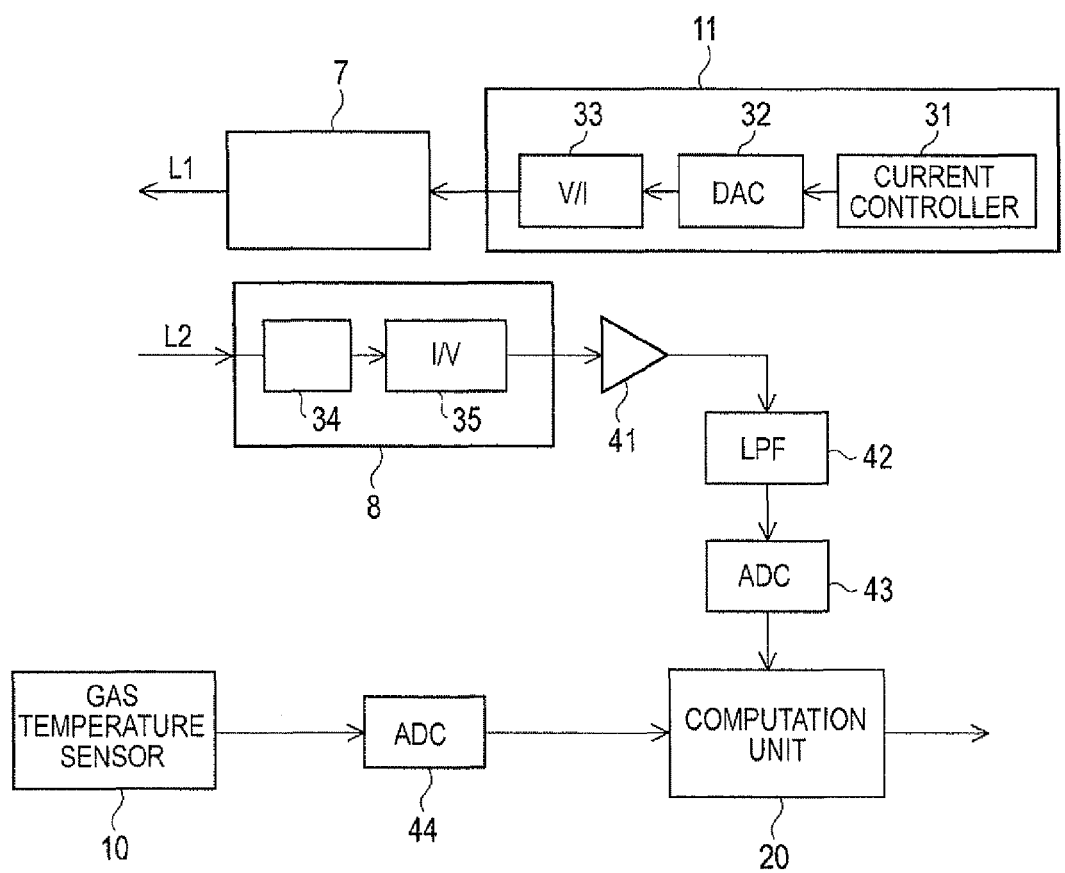
FIG. 4 shows a schematic view of the control system and the signal processing system of the first embodiment as a moisture measurement apparatus.

The photodetector 8 includes photoelectric conversion device 34 such as a photodiode and an I/V conversion amplifier 35 for converting the current signal obtained by the photoelectric conversion device into a voltage signal (FIG. 4). Moisture (interfering moisture) inside the optical chamber is eliminated by a purge gas, dehumidifying agent and the like, and its partial pressure is reduced to an ignorable level.

Figure 5:
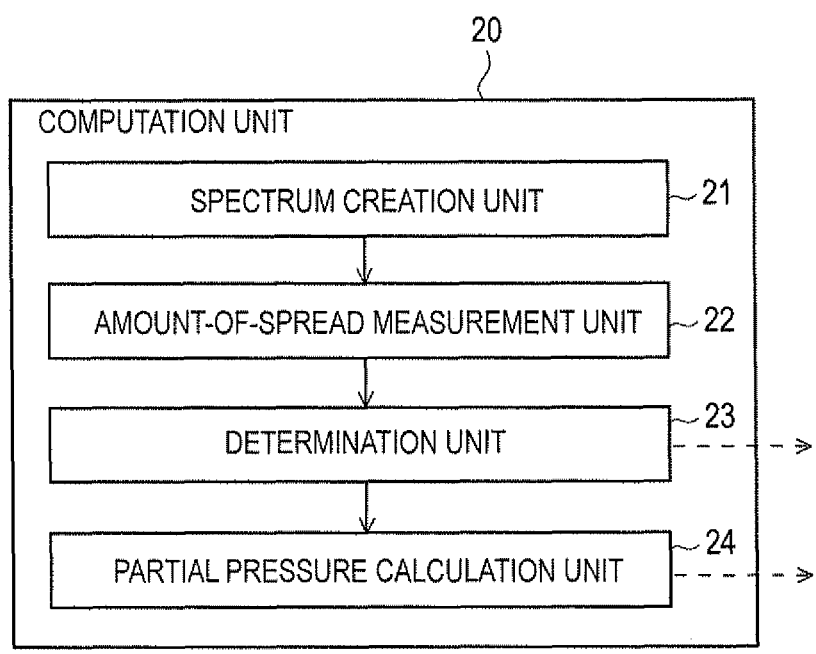
FIG. 5 shows a block diagram of the configuration of a computation unit of the first embodiment as a moisture measurement apparatus.

Unlike previous gas analyzers, the moisture measurement apparatus of the present embodiment is equipped only with a gas temperature sensor 10 and does not have a pressure sensor. Furthermore, the computation unit 20 includes: a spectrum creation unit 21 that uses detection signals from photodetector 8 to create the absorption spectrum of a specific gas; an amount-of-spread measurement unit 22 for measuring the amount of spread in the peak of the spectrum; a determination unit 23 for determining whether or not the amount of spread falls within a predetermined range; and a partial pressure calculation unit that uses equations (2), (5), (6) and (7), the intensity of the absorption spectrum for a predetermined wavelength and the temperature measured by gas temperature sensor 10 for calculating partial pressure $P_S$ of the water vapor (see FIG. 5). The results obtained by the abnormality detection unit 23 and the partial pressure calculation unit 24 are sent to an output unit 13 such as monitors and the like.

Platinum resistance thermometer sensors, thermistors, thermocouples and the like can be used as the gas temperature sensor 10.

In FIG. 3, laser beam L1 that is emitted by the wavelength variable laser 7 under the control of laser controller 11 passes through transparent window 5, enters sample cell 1 and is repeatedly reflected by reflection mirrors 3 and 4. With the optical path shown in FIG. 3, the laser beam traverses across gas flow path 2 and makes two round-trips between reflection mirrors 3 and 4. However, the optical system may be constructed so that more than two round-trips are made. As the laser beam traverses across the gas flow path 2, the laser beam is absorbed by moisture that is present in the gas. The laser beam L2 following the absorption by moisture as afore-described passes through transparent window 5 and returns into optical chamber 6 and reaches photodetector 8. The electrical signal that is output by photodetector 8 is processed to eliminate noise, undergo analog/digital conversion and the like and is input to the computation unit 20. Furthermore, the temperature of the gas to be measured in sample cell 1 is converted to an electrical signal by gas temperature sensor 10 and undergoes a predetermined signal processing after which the signal is input to the computation unit 20. After predetermined processes are performed based on these input signals by the computation unit 20, abnormalities in the measurement environment are detected, and the partial pressure of the specific gas is calculated. The results are then output to the output unit 13.

The control systems and signal processing systems for the different units of the present embodiment as a moisture measurement apparatus are described next with reference to FIG. 4.

The laser controller 11 includes current controller 31, digital/analog converter (DAC) 32 and voltage/current converter (V/I) 33. The DAC 32 converts the digital data that is output by current controller 31 for repeatedly sweeping the wavelength region close to the absorption spectrum of water molecules to a sweep voltage and outputs the sweep voltage. The sweep voltage is then converted to a current signal by V/I 33, and a driving current having a sawtooth pattern is provided to wavelength variable laser 7. This causes the wavelength variable laser 7 to emit a laser beam whose wavelength repeatedly changes with time over a predetermined wavelength range.

Laser beam L2 is received by photodetector 8 after the laser beam is first emitted by wavelength variable laser 7 and then absorbed by water molecules. In response to receiving the laser beam L2, the photodetector 8 outputs a voltage signal. The voltage signal is amplified by amplifier 41, noise components therein are removed by low-pass filter (LPF) 42, and the voltage signal is converted to digital values by analog/digital converter (ADC) 43. The digital values are then input to computation unit 20.

The temperature of the gas to be measured in sample cell 1 is converted to a voltage signal by gas temperature sensor 10. The voltage signal is converted to digital values by ADC 44, and the digital values are input to computation unit 20.

The specific processing procedure that is performed by computation unit 20 is described next with reference to the flowchart shown in FIG. 6.

Figure 7A:
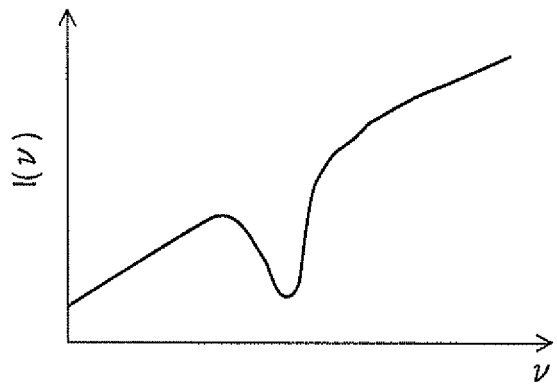
FIG. 7(a) shows a schematic view of the spectrum waveform of transmission light intensity I that is detected by the photoreceptor of the first embodiment as a moisture measurement apparatus; (b) shows a schematic view of the laser beam intensity $I_0$ prior to absorption by water molecules and created by approximation using data in the non-absorption bands on both sides of the peak; and (c) shows a schematic view of the spectrum for absorption amount $A=\ln(I/I_0)$.
Figure 7B:
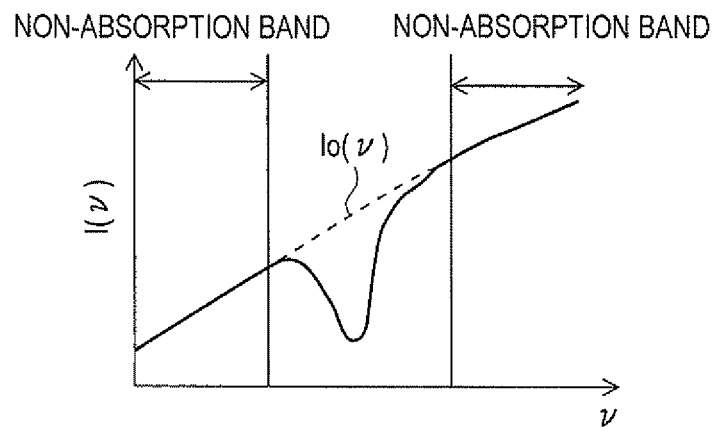

First, in step A1, an absorption spectrum is created by spectrum creation unit 21 based on the emission wavelength of the laser beam and the signal strength of the transmitted light that is input from ADC 43. The absorption spectrum is created in the following way. First, as shown in FIG. 7(a), a transmission light intensity I(v) spectrum is created. Next, using the data for transmission light intensity I(v) in the non-absorption band, which is not affected by absorption by water molecules, $I_0(v)$ is created by approximation (see FIG. 7(b)). Then, using the data for transmission light intensity I(v) and $I_0(v)$ obtained by approximation, a spectrum (absorption spectrum) showing absorption amount A is created (FIG. 7(c)).

Figure 7C:
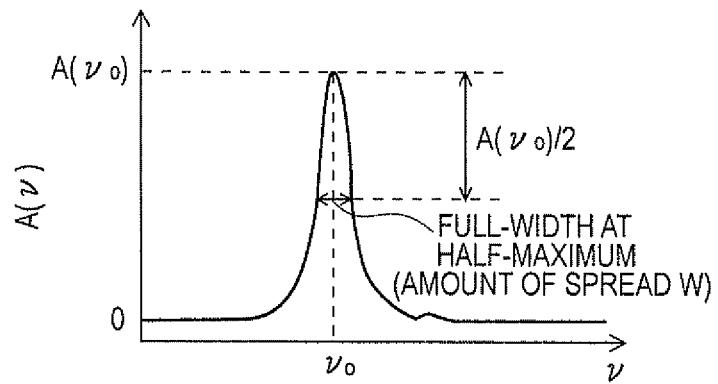

Next, the amount-of-spread measurement unit 22 measures the amount of spread W for the peak in the absorption spectrum shown in FIG. 7(c) (step A2). With the present embodiment, full-width at half-maximum of the peak is used as the amount of spread. However, any quantitative measurement that allows determining a change in peak width such as half-width at half-maximum or the width of the tails at either sides of the peak can be used as the measure of the amount of spread.

In step A3, full-width at half-maximum W that was measured in step A2 as indicating the amount of spread is used by determination unit 23 for determining whether or not the measurement environment is in a high-vacuum region. As shown in FIG. 2 and represented by equations (4) and (8), if the pressure of the gas to be measured is in a pressure region higher than the high-vacuum region, the width of the peak of the absorption spectrum monotonically increases with increased pressure. This means that a threshold value D for the amount of spread can be defined in advance, and the amount of spread W measured by the amount-of-spread measurement unit 22 can be compared against the threshold value D to determine whether or not the measurement environment is in a predetermined high-vacuum region. Specifically, if W>D, the measurement environment is determined to be not in a high-vacuum region, and abnormality is output to the outside via output unit 13 (step A4). If that is not the case, the measurement environment is determined to be in a high-vacuum region, and the partial pressure is calculated by the partial pressure calculation unit 24 (step A5).

If the temperature of the gas to be measured varies greatly, the threshold value D has to be defined taking into account the temperature change. In this case, the temperature that is measured by gas temperature sensor 10 can be substituted in equation (7) so that $D=2\gamma_{ED}$. This allows a threshold value to be defined that corresponds to the change in temperature.

Even though, with the present embodiment, the high-vacuum region was defined to be a pressure region of less than approximately 1 Torr, this value is not a specific limitation. For example, if the change in the shape of the peak or the half-width at half-maximum of the absorption spectrum caused by a change in pressure is not significant, a wider pressure region can be defined as the high-vacuum region.

Figure 8:
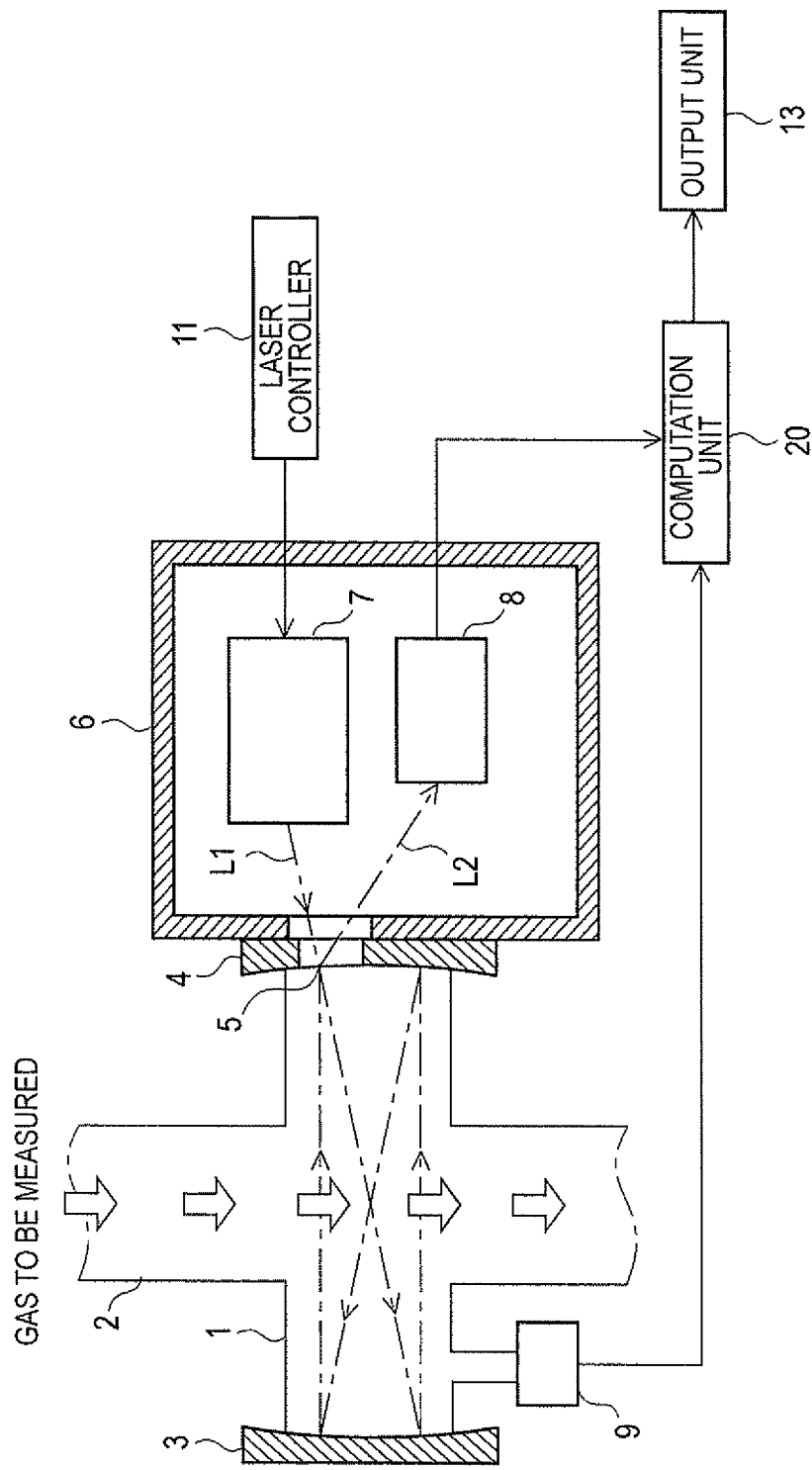
FIG. 8 shows a schematic view of a first variation of the configuration of the first embodiment as a moisture measurement apparatus.

A first variation of the present embodiment as a moisture analysis apparatus is shown in FIG. 8. Unlike the moisture analysis apparatus of the afore-described embodiment, the moisture analysis apparatus of the first variation is configured with a pressure sensor 9 but not with a gas temperature sensor 10. Other than this difference, the configuration is the same as that of the afore-described embodiment.

By using the moisture analysis apparatus having the configuration shown in FIG. 8, so long as the gas temperature is known and is constant, abnormalities in gas temperature can be detected by comparing the amount of spread W against a threshold value D even for a measurement environment where the pressure of the gas to be measured changes from atmospheric pressure to a high-vacuum region.

Figure 9:
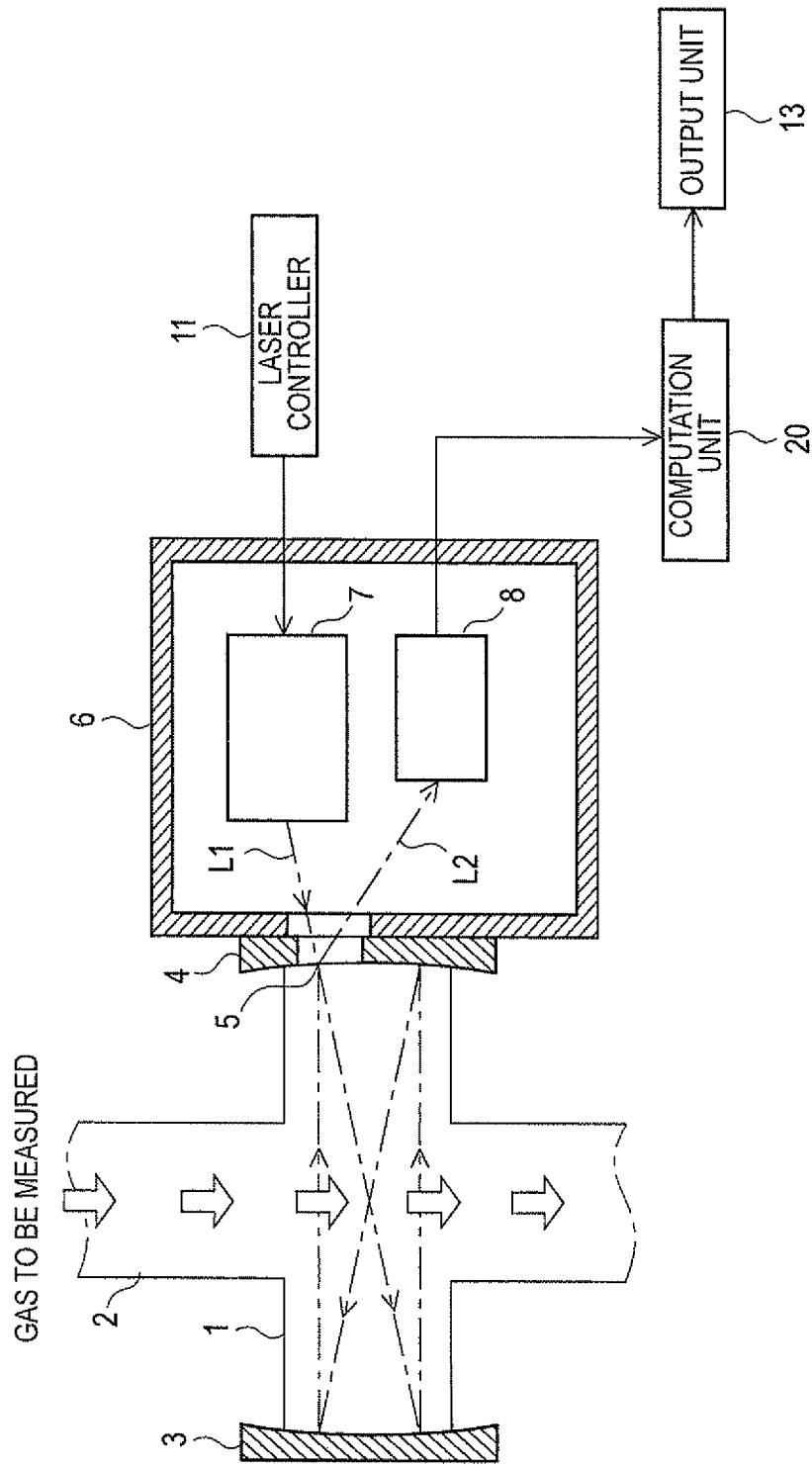
FIG. 9 shows a schematic view of a second variation of the configuration of the first embodiment as a moisture measurement apparatus.

Furthermore, if the pressure of the gas to be measured is in a high-vacuum region and the gas temperature is known in advance, even a gas temperature sensor can be eliminated from the device configuration as shown in the second variation shown in FIG. 9 while detecting abnormalities in either the pressure or the temperature of the gas to be measured.

Embodiment 2

The afore-described embodiments were capable of notifying to the outside of just abnormalities that are detected when the amount of spread W does not fall within a predetermined range. In doing this, it is also possible to configure the device to calculate the pressure of the gas to be measured from the measured values of temperature and the amount of spread and to output the results to an output unit 13. This is explained with reference to the block diagram shown in FIG. 10 and the flowchart shown in FIG. 11.

Figure 10:
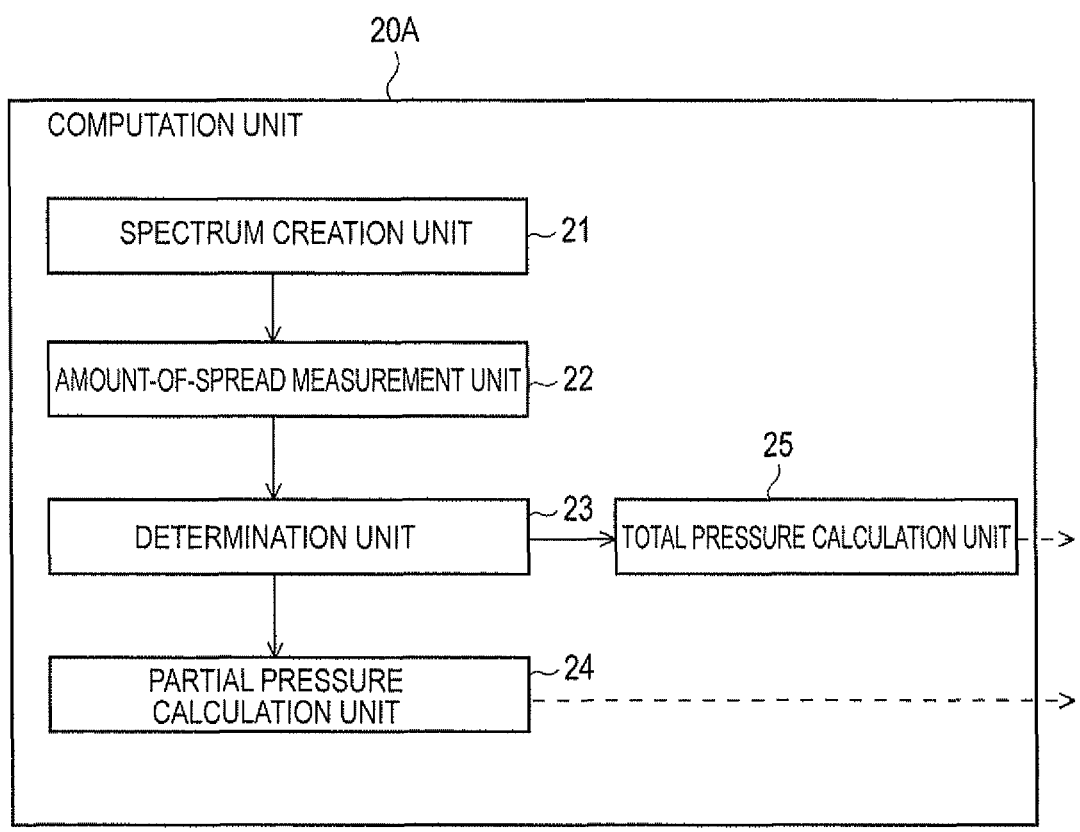
FIG. 10 shows a block diagram of the configuration of a computation unit of the second embodiment of the present invention as a moisture measurement apparatus.
Figure 11:
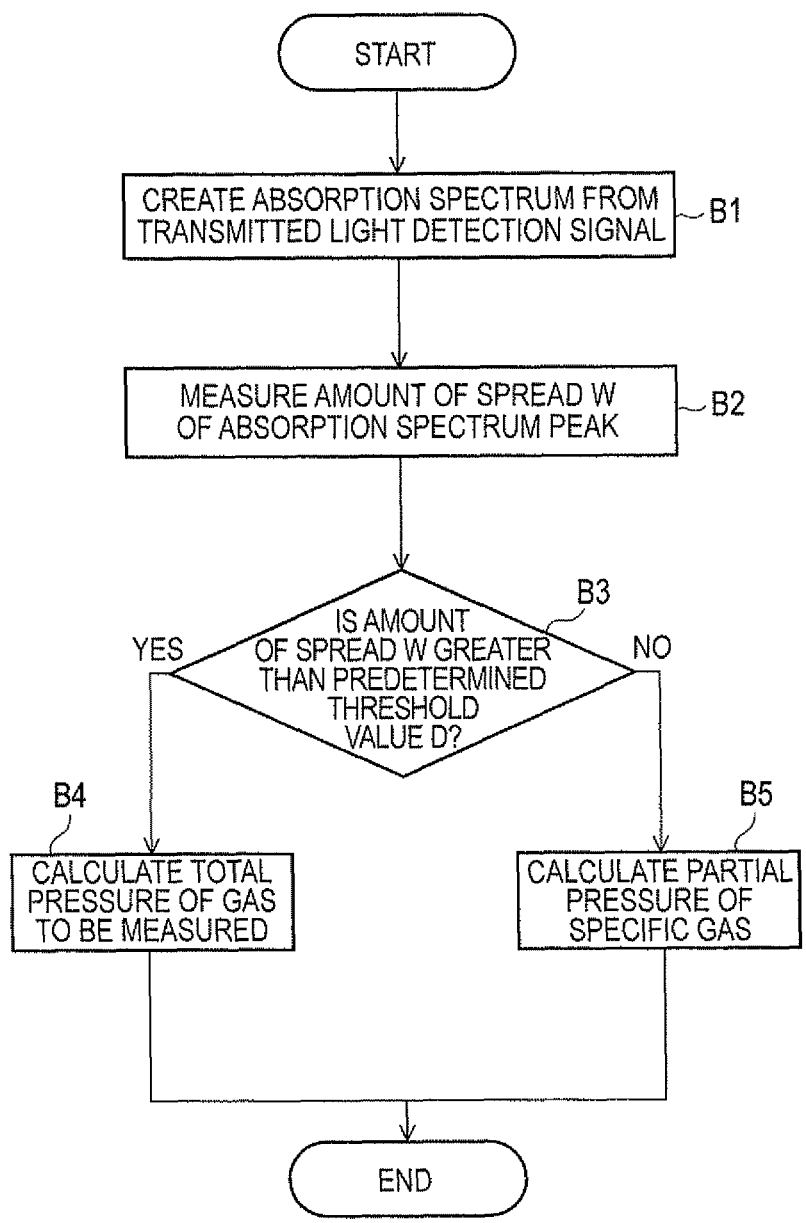
FIG. 11 is a flowchart showing the process flow in the computation unit of the second embodiment of the present invention as a moisture measurement apparatus.

The configuration of the moisture measurement apparatus of this embodiment is the same as that of the first embodiment shown in FIG. 3 except for the fact that the computation unit 20 is replaced by computation unit 20A shown in FIG. 10. The configuration of computation unit 20A is the same as that of computation unit 20 except for the new addition of a total pressure calculation unit 25.

The specific processing procedure that is used by computation unit 20A in this embodiment as a moisture measurement apparatus is described next. The processing procedure used by computation unit 20a in this embodiment is substantially the same as that of computation unit 20 in the first embodiment but is different in that if an abnormality is detected in step B3, the total pressure calculation unit 25 uses the measured values of amount of spread W and temperature T to calculate pressure P of the gas to be measured (step B4). Because the fact that an abnormality is detected here means that the pressure of the gas to be measured has changed from a high-vacuum region to an intermediate pressure region, if full-width at half-maximum is used as the measure of the amount of spread W as in the first embodiment, W/2 becomes equal to Voigt width $\gamma_V$. Hence, pressure P of the gas to be measured can be calculated based on temperature T that is measured by gas temperature sensor 10, Voigt width $\gamma_V=W/2$ and equations (3), (6) and (8).

Figure 12:
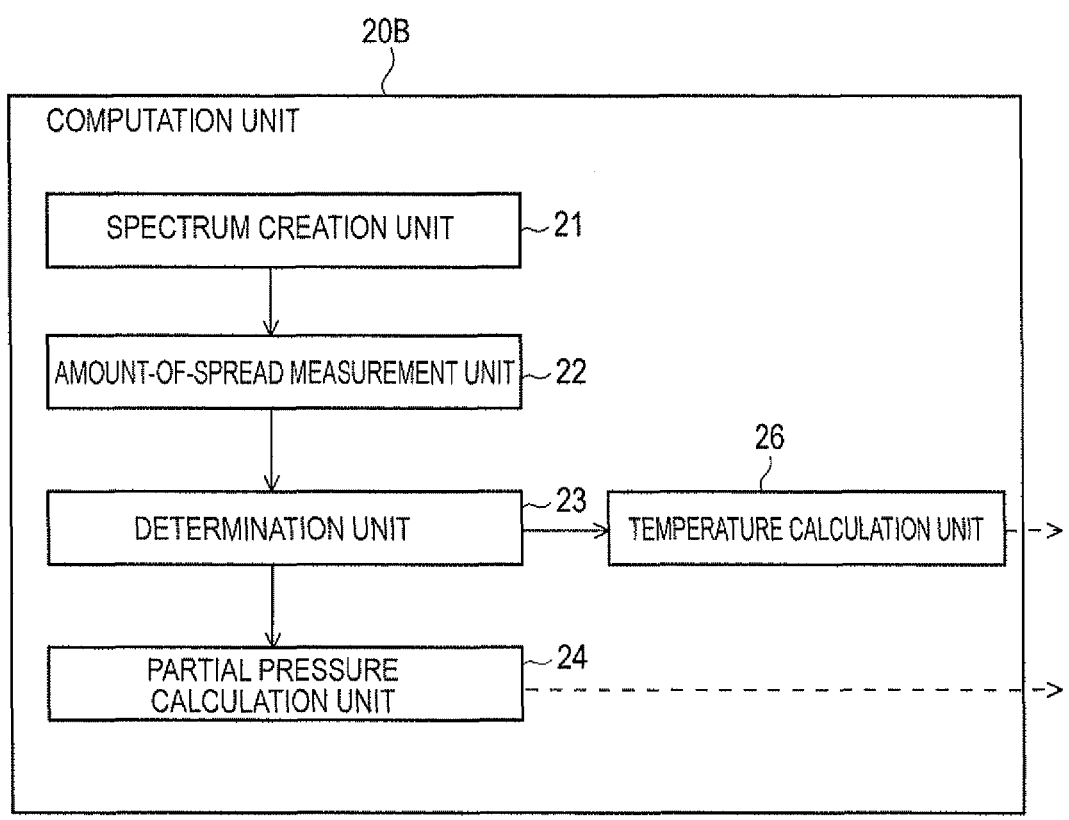
FIG. 12 shows a block diagram of the configuration of a computation unit of a variation of the second embodiment of the present invention as a moisture measurement apparatus.

Just as with the afore-described embodiment, even with the first variation of the configuration of the first embodiment, gas temperature T can be calculated from the measured values of amount of spread W and pressure P. The device configuration of this variation is substantially the same as that shown in FIG. 8, and the only difference is the replacement of computation unit 20 with computation unit 20B shown in FIG. 12. Furthermore, the only change that is made with computation unit 20B is the replacement of total pressure calculation unit 25 identified in the afore-described embodiment with temperature calculation unit 26.

With this variation of the moisture analysis apparatus, the equation that is used by the temperature calculation unit 26 for the calculation of temperature is selected from among equations (4), (7) and (8) depending on the pressure region to which the pressure that is measured by pressure sensor 9 belongs. Then, based on the selected equation, temperature T is calculated based on the measured values of pressure P and amount of spread W.

Embodiment 3

Figure 13A:
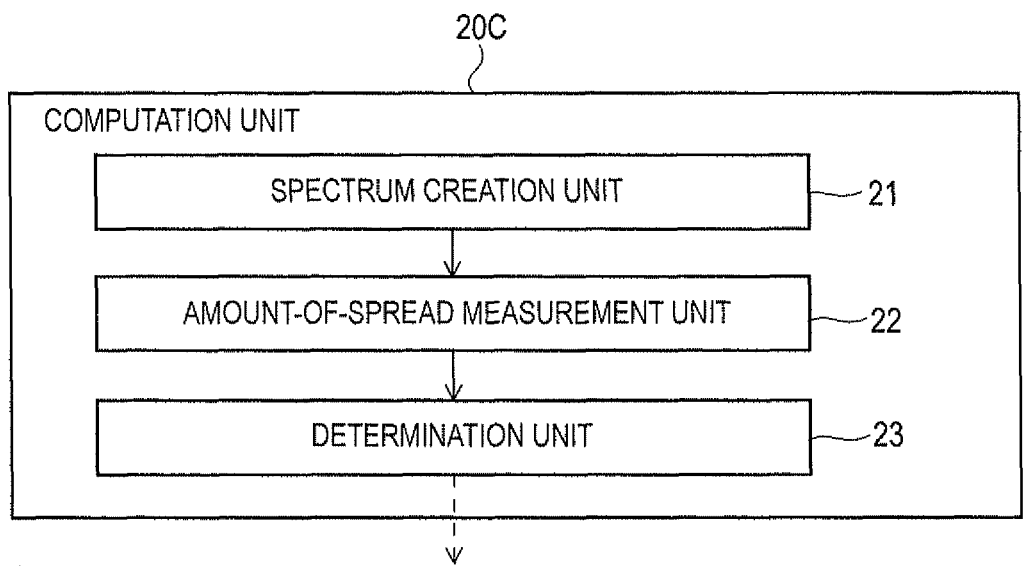
FIG. 13 shows a block diagram of the configuration of a computation unit of a vacuum level determination device according to the present invention.
Figure 13B:
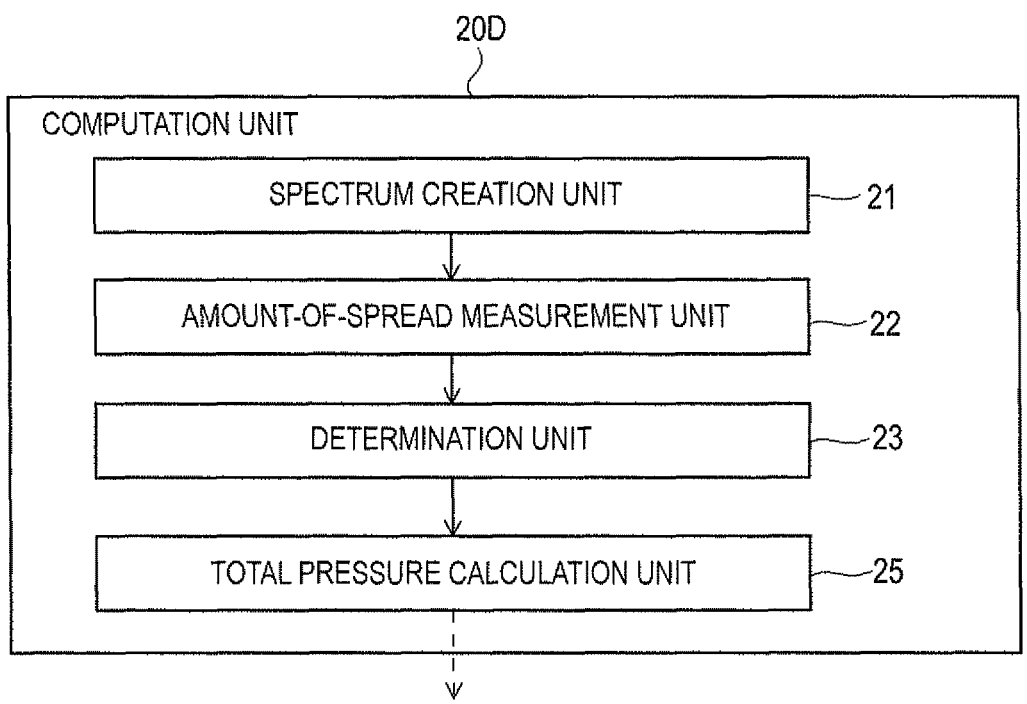

The first and second embodiments of the gas analyzers according to the present invention can also be used as a vacuum level determination device for determining the level of vacuum inside sample cell (measurement space) 1. The configuration of the vacuum level determination device of this embodiment is substantially the same as that of the first and second embodiments of the gas analyzer except for the elimination of partial pressure measurement unit 24 from the configuration of computation unit 20 or 20A as shown in FIG. 13(a) showing computation unit 20C or FIG. 13(b) showing computation unit 20D. The vacuum level determination device is capable of constantly monitoring, in a non-contact manner and with a high time resolution, whether or not the pressure within a sample cell (measurement space) 1 falls within a predetermined high-vacuum region.

DESCRIPTION OF THE NUMERICAL REFERENCES

1. Sample cell
2. Gas flow path
3. Reflection mirror
5. Transparent window
6. Optical chamber
7. Wavelength variable laser (laser irradiation unit)
8. Photodetector (photoreceptor)
9. Pressure sensor
10. Gas temperature sensor
11. Laser controller
12, 20, 20A, 20B, 20C, 20D. Computation unit
13. Output unit
21. Spectrum creation unit
22. Amount-of-spread measurement unit
23. Determination unit
24. Partial pressure calculation unit
25. Total pressure calculation unit
26. Temperature calculation unit
31. Current controller
32. Digital/analog converter (DAC)
33. Voltage/current converter (V/I)
34. Photoelectric conversion device
35. I/V conversion amplifier
41. Amplifier
42. Low-pass filter (LPF)
43, 44. Analog/digital converter (ADC)

What is claimed is:

1. A gas analyzer comprising:
an irradiation means for irradiating a laser beam onto a gas to be measured;
a laser control means for controlling said laser irradiation means so that the emission wavelength of said laser beam changes over a predetermined wavelength range that includes the center wavelength of the absorption spectrum of a specific gas that is included in said gas to be measured; and
a light-receiving means for receiving the laser beam that has been transmitted through said gas to be measured;
and further comprising:
a) a spectrum creation means for creating an absorption spectrum from detection signals of the laser beam received by said light-receiving means;
b) an amount-of-spread measurement means for measuring the amount of spread of a peak of said absorption spectrum; and
c) a determination means for determining whether or not said amount of spread falls within a predetermined range which in turn determines whether or not pressure of said gas to be measured falls within a high vacuum region where the absorption spectrum depends solely on temperature and not on pressure.

2. The gas analyzer according to claim 1 wherein, if said amount of spread does not fall within a predetermined range, the pressure of said gas to be measured is calculated from measured values of said amount of spread and temperature.

3. The gas analyzer according to claim 1 wherein, if said amount of spread does not fall within a predetermined range, the temperature of said gas to be measured is calculated from measured values of said amount of spread and pressure.

4. A vacuum level determination device for determining whether or not pressure within a measurement space falls within a predetermined high-vacuum region and comprising:
   a) a laser irradiation means for irradiating a laser beam into said measurement space;
   b) a laser control means for controlling said laser irradiation means so that the emission wavelength of said laser beam changes within a predetermined wavelength range;
   c) a light-receiving means for receiving a laser beam that has been transmitted through said measurement space;
   d) a spectrum creation means for creating an absorption spectrum from detection signals of laser beam that is received by said light-receiving means;
   e) an amount-of-spread measurement means for measuring the amount of spread of a peak of said absorption spectrum; and
   f) a determination means for determining whether or not said amount of spread falls within a predetermined range which in turn determines whether or not pressure of said gas to be measured falls within a high vacuum region where the absorption spectrum depends solely on temperature and not on pressure.

5. The vacuum level determination device according to claim 4 wherein, if said amount of spread does not fall within a predetermined range, the pressure within said measurement space is calculated from measured values of said amount of spread and temperature.

6. The vacuum level determination device according to claim 4 wherein said high-vacuum region is a region with a pressure of no more than 1 Torr.

* * * * *